United States Patent [19]
Madsen et al.

[11] Patent Number: 5,853,377
[45] Date of Patent: Dec. 29, 1998

[54] SYSTEM AND METHOD FOR MONITORING AND ANALYZING DYNAMIC NUTRITIONAL STATUS IN PATIENTS WITH CHRONIC DISEASE

[75] Inventors: David C. Madsen, Libertyville; Chris Kruzel, Chicago, both of Ill.; Susan Trimbo, Madison, N.J.; Theresa Voss, Antioch, Ill.; Kathryn Hennessy, Arlington Heights, Ill.; Carol Siegel, Vernon Hills, Ill.; Hugh N. Tucker, Barrington, Ill.

[73] Assignee: Nestec S.A., Vevey, Switzerland

[21] Appl. No.: 843,986

[22] Filed: Apr. 17, 1997

[51] Int. Cl.⁶ .................................................. A61B 5/103
[52] U.S. Cl. .......................................................... 600/587
[58] Field of Search ...................................... 600/587, 595

[56] References Cited

U.S. PATENT DOCUMENTS

| | | | |
|---|---|---|---|
| 4,629,015 | 12/1986 | Fried et al. | 600/587 |
| 4,803,625 | 2/1989 | Fu et al. | 126/906 |
| 4,869,266 | 9/1989 | Taylor et al. | 600/587 |
| 4,951,197 | 8/1990 | Mellinger | 600/587 |
| 5,022,261 | 6/1991 | Wolfson et al. | 73/149 |
| 5,435,315 | 7/1995 | McPhee et al. | 600/587 |
| 5,474,083 | 12/1995 | Church et al. | 600/595 |
| 5,494,046 | 2/1996 | Cross | 600/595 |
| 5,544,649 | 8/1996 | David et al. | 600/587 |
| 5,628,328 | 5/1997 | Nissen et al. | 600/587 |

*Primary Examiner*—Max Hindenburg
*Assistant Examiner*—Charles Marmor, II
*Attorney, Agent, or Firm*—Hill & Simpson

[57] ABSTRACT

A system and a method are provided for monitoring a patient. The system receives information relating to weight and/or LBM of a patient as well as other clinical and medical variable may be input relating to the patient. Warning levels or alert levels are input to the system such that a patient or clinician is immediately notified upon the patient reaching such levels. The system provides local transmission to a patient or remote transmission to, for example, a clinician of the patient or the like. The system and method are particularly useful for patients with chronic disease such that the dynamic nutritional status may be closely monitored and analyzed and ultimately addressed when significant changes occur.

19 Claims, 2 Drawing Sheets

SYSTEM AND METHOD FOR MONITORING AND ANALYZING DYNAMIC NUTRITIONAL STATUS IN PATIENTS WITH CHRONIC DISEASE

BACKGROUND OF THE INVENTION

The present invention generally relates to a system and a method for monitoring a patient. More specifically, the present invention relates to a system and a method for monitoring and analyzing dynamic nutritional status in patients with chronic disease.

It is, of course, generally known to monitor weight of a patient. Weight can be periodically monitored either by a patient or by a clinician or physician. However, often weight is monitored too infrequently, and only drastic changes in weight are noticed. This can be particularly problematic for patients suffering from chronic diseases.

That is, weight changes in patients with chronic diseases, such as HIV, AIDS, oncology, cystic fibrosis, inflammatory bowel disease and the like, are particularly important to monitor. What may be insignificant decreases in weight for most individuals may cause harmful effects in chronically ill patients. However, most individuals and many doctors or clinicians monitoring such changes only react to severe weight loss or weight gain.

Furthermore, the effects of weight change on lean body mass (LBM) of a patient are often overlooked. In fact, the weight of an individual may not change, but the LBM may be affected due to other factors, particularly with chronically ill patients. More specifically, many other clinical and medical variables, such as anthropometrics, changes in stooling and food intake, occurrence and type of infections, medications or CD4 data may affect body weight and/or LBM.

Still further, often changes in body weight or LBM are discovered too late. Again, this is particularly troublesome for patients suffering from chronic disease. However, if weight and/or LBM is continuously, or at least frequently, tracked, dangerous levels of loss and/or gain, however minor, can be brought to the patient's attention or to the attention of the patient's clinician or physician.

A need, therefore, exists for an improved system and method for monitoring and analyzing dynamic nutritional status in patients. Particularly, a need exists for a system and method for monitoring and analyzing dynamic nutritional status in patients with chronic disease such that the patient can be notified of any abnormal losses or gains in body weight and/or LBM.

SUMMARY OF THE INVENTION

The present invention provides a system and a method for monitoring body weight and/or LBM of a patient. The present invention further relates to a system and method for monitoring and analyzing dynamic nutritional status in patients with chronic disease.

In an embodiment of the present invention, a system is provided for monitoring a patient. The system has input means for entering information relating to the patient. Memory means stores pre-selected conditions relating to physical changes of the patient. Processing means receives the information and compares the information to the pre-selected conditions and produces a signal indicative of a result of the comparison. An output means receives the signal from the processing means.

In an embodiment, the input means is a scale that measures weight of the patient.

In an embodiment, the input means is capable of receiving clinical and medical variables of the patient.

In an embodiment, the input means is capable of receiving information relating to LBM of the patient.

In an embodiment, the output means is a video display.

In an embodiment, the output means is an alarm.

In an embodiment, means for remotely transmitting the signal to the output means is provided.

In an embodiment, the memory means stores informational discourses.

In another embodiment of the present invention, a method is provided for monitoring a patient. The method comprises the steps of: entering information relating to the patient and producing an input signal indicative thereof; storing pre-selected conditions relating to physical changes of the patient; comparing the input signal to the pre-selected conditions; and producing an output signal indicative of a result of the comparison.

In an embodiment, the information relates to weight of the patient.

In an embodiment, the information relates to LBM of the patient.

In an embodiment, the method further comprises the step of transferring the output signal to an output device. The output device is a video display or an alarm.

In an embodiment, the output signal is remotely transferred.

In an embodiment, the method further comprises the step of predicting a time at which one of the pre-selected conditions will be attained.

In an embodiment, the information is directly input by the patient.

In an embodiment, the method further comprises the step of calculating loss of LBM without abnormal changes in weight of the patient.

In an embodiment, the method further comprises the step of providing suggestions to the patient based on the output signal.

In an embodiment, the method further comprises the step of providing informational discourses to the patient based on the output signal.

It is, therefore, an advantage of the present invention to provide a system and method for monitoring a patient.

Yet another advantage of the present invention is to provide a system and a method for monitoring a patient with chronic disease.

Yet another advantage of the present invention is to provide a system and a method for monitoring changes in weight of a patient.

Yet another advantage of the present invention is to provide a system and a method for monitoring changes in LBM of a patient.

And, another advantage of the present invention is to provide a warning signal to a patient and/or a patient's clinician or physician as a result of changes in weight and/or LBM.

A still further advantage of the present invention is to provide a system and a method that remotely transmits information regarding a patient to a patient's physician or clinician.

Yet another advantage of the present invention is to provide a system and a method that provides informational discourses to a patient as a result of changes in weight or LBM of the patient.

Moreover, an advantage of the present invention is to provide a system and a method that predicts pre-selected warning zones in which a patient will attain actual amounts of weight loss or weight gain and/or loss or gain of LBM.

A still further advantage of the present invention is to provide a system and a method for notifying a patient of loss of LBM when body weight remains normal.

A still further advantage of the present invention is to provide a display of change in weight over time for visualization by a patient and/or his physician or clinician.

Moreover, an advantage of the present invention is to provide a system and a method for monitoring and analyzing weight changes for a variety of chronic diseases including, but not limited to, HIV, AIDS, oncology, cystic fibrosis, inflammatory bowel disease and other GI disorders, self-imposed weight reduction programs or rehabilitation aiming for weight gain.

These and other advantages of the present invention are described in, and will be apparent from, the detailed description of the presently preferred embodiments and from the drawings.

DETAILED DESCRIPTION OF THE PRESENTLY PREFERRED EMBODIMENTS

The present invention provides a system and method for detecting changes in body weight and/or lean body mass (LBM) of a patient. More specifically, the present invention provides a system and method for monitoring and analyzing dynamic nutritional status in patients with chronic diseases through analysis of changes in body weight and/or LBM of the patients.

Figure 1:
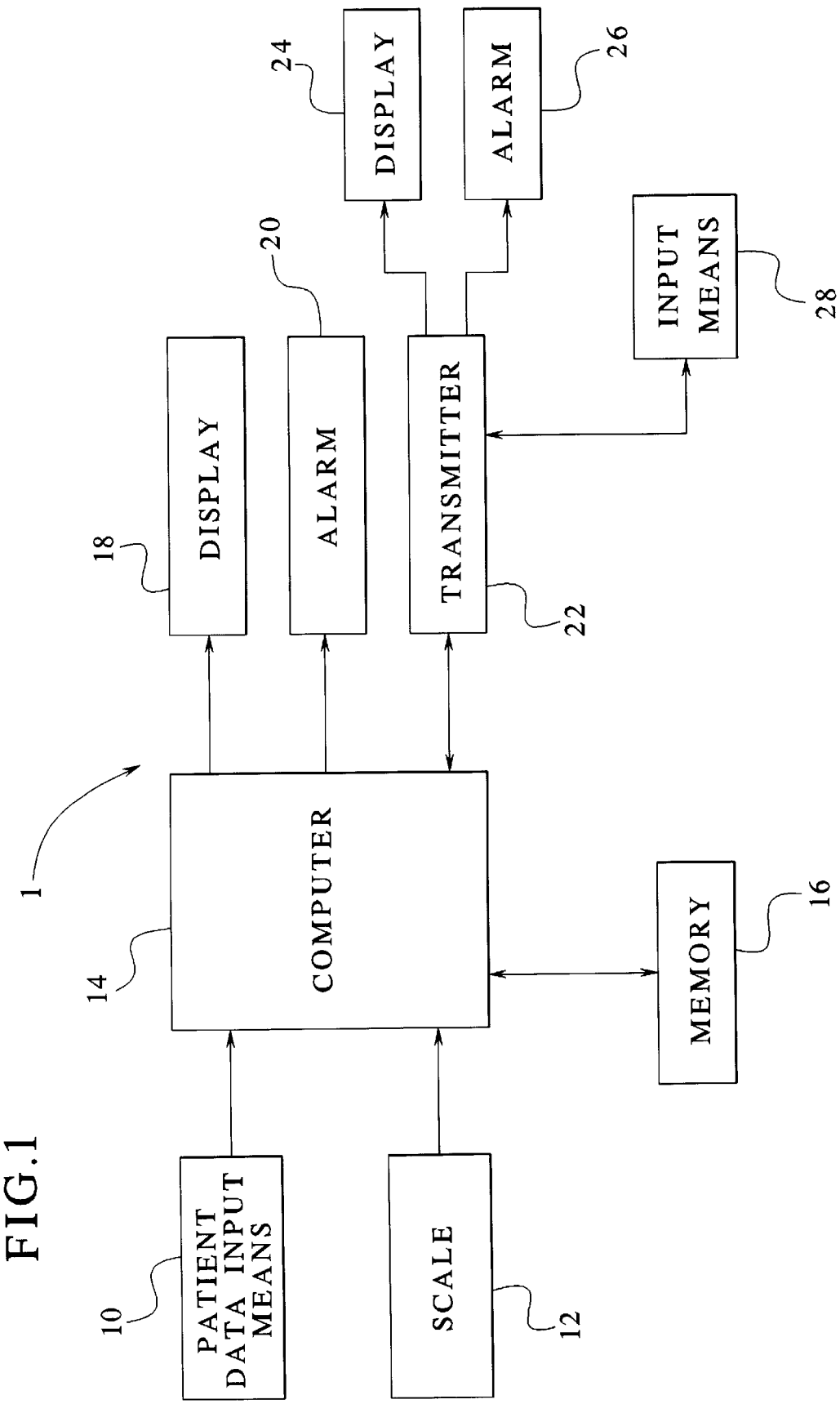
FIG. 1 illustrates a black box diagram of a system for analyzing a patient in an embodiment of the present invention.

Referring now to FIG. 1, a black box diagram of the components necessary for monitoring and analyzing dynamic nutritional status in patients is illustrated. As previously set forth, the system 1 is designed for use by a patient at home or in a clinical setting or by a clinician.

The system 1 includes an input means 10 for entry of patient data, such as, for example, body weight of the patient. The input means 10 may be, for example, a keyboard that allows entry of data by the patient or any other individual. In addition, lean body mass (LBM) may also be calculated by the system 1 through an input by the patient via the patient data input means 10. Lean body mass, of course can be calculated by any means known in the art based on necessary input for computing the same. Other clinical and medical variables may also be entered, such as, but not limited to, anthropometrics, changes in stooling and food intake, occurrence and/or type of infections, medications, CD4 data and information as to whether the patient is HIV/AIDS.

Alternatively, a scale 12 may be connected to the system 1 such that data relating to patient weight may be directly fed from the scale 12 via an electrical input or infrared signals from the scale 12 to a computer 14. The computer 14 includes memory 16 and/or is supplemented with memory 16 to store specific patient-related information and other desired data. In a preferred embodiment, the computer 14 is PC-based.

In a preferred embodiment, the patient and/or clinician pre-select a change in body weight or LBM that is viewed as an "ALERT" or "WARNING" level that requires intervention. The warning levels are input via the input means 10 and stored in the memory 16 of the computer 14. The computer 14 tracks weight of the patient continuously through the input by the patient through the input means 10 or through direct input from the scale 12. By continuous or periodic tracking of the weight, the computer 14 predicts when the warning level will be attained based on the course in which the patient's weight is following, should that course continue.

In addition, the computer 14 may notify a patient directly through use of a display 18 of an impending warning level or of a warning level being reached. Alternatively, or in addition to, a signal may be sent to a visual or audio alarm 20 for immediate recognition by the patient.

A clinician or physician of the patient may also be remotely connected to outputs from the computer 14 via a remote transmitter 22. The remote transmitter 22 transfers signals from the computer 14 to a display 24 and/or alarm 26 in, for example, an office of the clinician.

In addition to the foregoing, the computer 14 also tracks loss and subsequent regaining of weight by a patient and keeps track of LBM that was likely not repleted to factor the same into subsequent calculations. A patient is then notified via the display 18 and/or the alarm 20 every time a loss and regain cycle has occurred including the number of times that the cycle has occurred. The computer 14 may be further programmed to detect significant decreases in body weight or LBM and, when those changes occur, the display 18 suggests to the patient to contact a clinician.

Other features are also programmed into the computer 14 to determine the significance of drastic changes in body weight or LBM. For example, the computer 14 may prompt a patient to input information as to whether an infection has occurred or whether catabolic events or symptoms, such as a fever, may be present. The computer 14 may also render nutritional advice to a patient with respect to what types of food should be eaten. In addition, when, how, and how much nutrition is required by a particular patient may also be provided to the patient by the computer 14. A physician may also be provided with an input means 28 such that the clinician or physician may remotely transmit information to the patient making recommendations based on observed changes in weight or LBM of the patient.

In the memory 16 of the computer 14, additional information may be provided regarding basic nutrition, nutrition for a patient's disease state, and/or information as to modifications of intake using specific foods and supplements. This information is stored in the memory 16 and may be directly requested by the patient and subsequently displayed or may be automatically output as a result of a change in a patient's condition.

Often, weight change is very gradual in a patient and, therefore, such changes are often only noticed with difficulty and careful attention. The present invention overcomes this problem by pre-selecting warnings or alert zones wherein specific changes in weight or LBM immediately alert the patient and/or clinician before reaching dangerous or troublesome levels. In addition, body weight often stays normal or very little fluctuation occurs; the system 1 of the present invention detects the loss of LBM even under conditions in which body weight is maintained. That is, the computer 14 is programmed to calculate, notify, and predict LBM deficits as a result of inputs to the computer 14 that may affect the LBM of a patient.

The display 18 of the present invention may also provide graphic displays of changes in weight or LBM over time to allow visualization of trends. Hard copies of displayed information may, of course, be output, and printing may also may be implemented by one of ordinary skill in the art.

Figure 2:
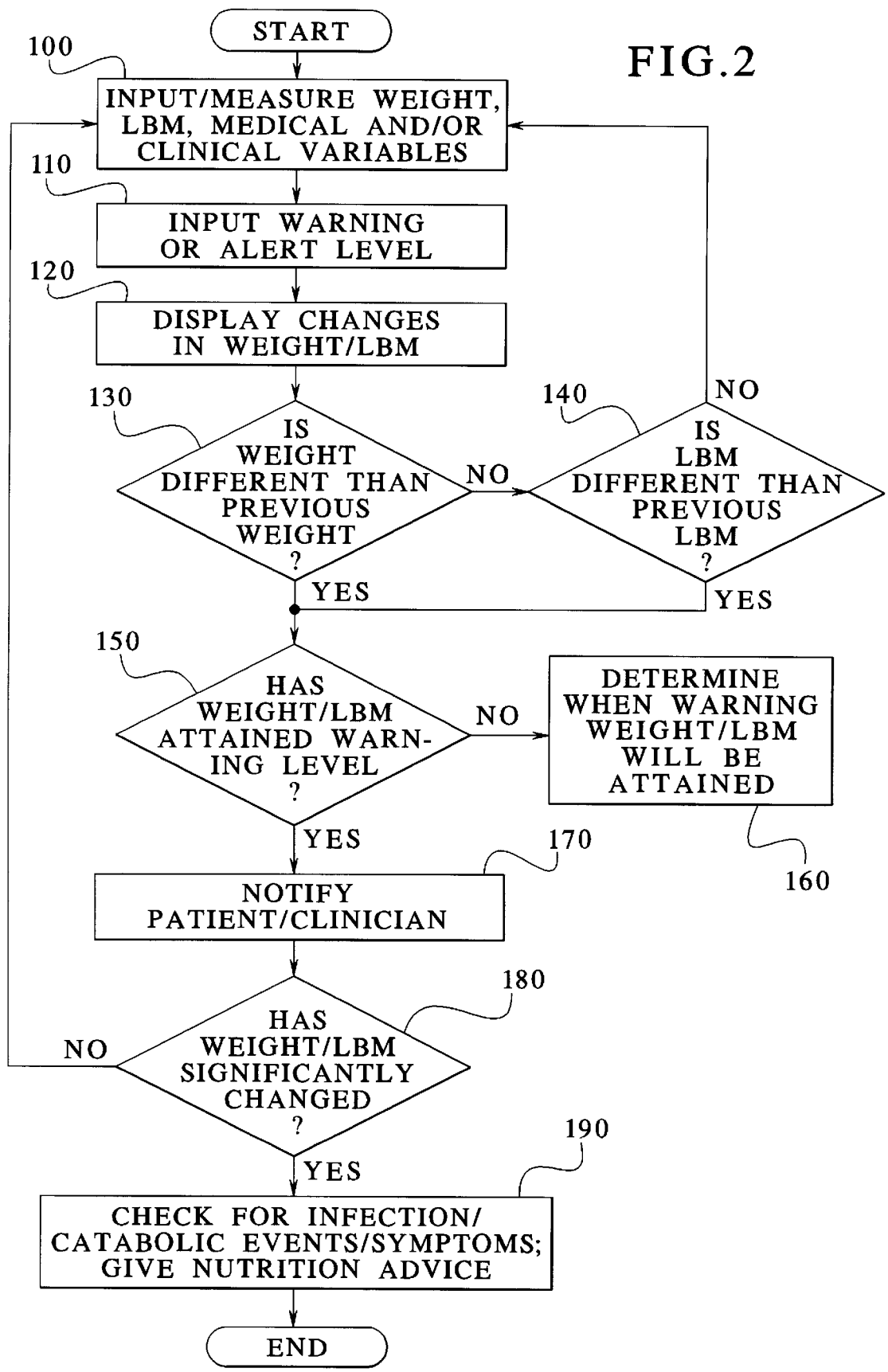
FIG. 2 illustrates a flow chart of an embodiment of the steps necessary for monitoring and analyzing changes in weight and/or LBM of a patient.

FIG. 2 generally illustrates a flow chart of the steps that the system 1 of FIG. 1 may follow to monitor and analyze patients. The system, begins by inputting or measuring weight of a patient at step 100. In addition, medical variables and/or clinical variables may be input as set forth and described above. At step 110, warning levels or alert levels may be input for changes in body weight and/or LBM that requires notification of the patient. A display of changes in weight or LBM may be continuously displayed as shown at step 120.

At step 130, a determination is made as to whether weight is different than previous weight. If not, at step 140, the system, determines if LBM or another condition of the patient is different than the previous condition of the patient based on the input weights and clinical and medical variables. If the LBM or other critical condition has changed as determined at step 140, a determination is made as to whether the weight or LBM has attained a warning level. If not, a determination may be made when the warning weight or LBM will be attained at step 160, or, if the same has already been attained, the patient and/or clinician is notified as identified at step 170. The system also determines whether the weight or LBM has significantly changed at step 180, and, if so, at step 190, a number of checks may be made including checks for infection, catabolic events, and/or patient symptoms indicative of the same. In addition, at step 190, nutritional advice for the patient including specific nutritional information for the patient's particular disease state may be provided.

The present invention may be applied to any disease or condition where weight or LBM changes are likely, whether the changes are positive or negative. The present invention is particularly useful for patients with HIV, AIDS, oncology, cystic fibrosis, inflammatory bowel disease and other GI disorders, self-imposed weight reduction programs or rehabilitation programs aiming for weight gain. Of course, any patient may use the system of the present invention, even for ordinary everyday monitoring of an individual.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

We claim:

1. A system for continuously monitoring, throughout an analysis, a patient having a chronic disease, the system comprising:

input means for entering information relating to the patient having the chronic disease wherein the input means is capable of receiving information relating to LBM of the patient having the chronic disease;

memory means for storing pre-selected conditions relating to physical changes of the patient;

processing means for receiving the information and comparing the information to the pre-selected conditions and producing a signal indicative of a result of the comparison; and output means for receiving the signal from the processing means.

2. The system of claim 1 wherein the input means is a scale that measures weight of the patient.

3. The system of claim 1 wherein the input means is capable of receiving clinical and medical variables of the patient.

4. The system of claim 1 wherein the output means is a video display.

5. The system of claim 1 wherein the output means is an alarm.

6. The system of claim 1 further comprising:

means for remotely transmitting the signal to the output means.

7. The system of claim 1 wherein the memory means stores informational discourses.

8. A method for continuously monitoring, throughout an analysis, a patient having chronic disease, the method comprising the steps of:

entering information relating to the patient having the chronic disease and producing an input signal indicative thereof wherein the information relates to LBM of the patient having the chronic disease;

storing pre-selected conditions relating to physical changes of the patient;

comparing the input signal to the pre-selected conditions; and producing an output signal indicative of a result of the comparison.

9. The method of claim 8 wherein the information relates to weight of the patient.

10. The method of claim 8 further comprising the step of:

transferring the output signal to an output device.

11. The method of claim 10 wherein the output device is a video display.

12. The method of claim 10 wherein the output device is an alarm.

13. The method of claim 8 wherein the output signal is remotely transferred.

14. The method of claim 8 further comprising the step of:

predicting a time at which one of the pre-selected conditions will be attained.

15. The method of claim 8 wherein the information is directly input by the patient.

16. The method of claim 8 further comprising the step of:

calculating loss of LBM without abnormal changes in weight of the patient.

17. The method of claim 8 further comprising the step of:

providing suggestions to the patient based on the output signal.

18. The method of claim 8 further comprising the step of:

providing informational discourses to the patient based on the output signal.

19. A method for continuously monitoring, throughout an analysis, a patient having chronic disease, the method comprising the steps of:

entering information relating to the patient having the chronic disease and producing an input signal indicative thereof;

storing pre-selected conditions relating to physical changes of the patient;

comparing the input signal to the pre-selected conditions;

producing an output signal indicative of a result of the comparison; and calculating loss of LBM without abnormal changes in weight of the patient having the chronic disease.

\* \* \* \* \*